(12) United States Patent
Legay et al.

(10) Patent No.: US 7,203,544 B2
(45) Date of Patent: Apr. 10, 2007

(54) DETECTION OF EVOKED POST-STIMULATION POTENTIALS, IN PARTICULAR ATRIAL POTENTIALS IN AN ACTIVE IMPLANTABLE MEDICAL DEVICE SUCH AS CARDIAC PACEMAKER, DEFRIBILLATOR, CARDIOVERTOR OR MULTISITE DEVICE

(75) Inventors: Thierry Legay, Fontenay les Bris (FR); Dominique Decoene, Jouars Pontchartrain (FR)

(73) Assignee: Ela Medical S.A.S., Montrouge (FR)

( * ) Notice: Subject to any disclaimer, the term of this patent is extended or adjusted under 35 U.S.C. 154(b) by 124 days.

(21) Appl. No.: 10/745,472

(22) Filed: Dec. 22, 2003

(65) Prior Publication Data

US 2004/0167577 A1  Aug. 26, 2004

(30) Foreign Application Priority Data

Dec. 26, 2002  (FR) .................................. 02 16724

(51) Int. Cl.
*A61N 1/37* (2006.01)
(52) U.S. Cl. ...................................... 607/28
(58) Field of Classification Search ............... 607/4–28
See application file for complete search history.

(56) References Cited

U.S. PATENT DOCUMENTS

| 4,498,478 | A | * | 2/1985 | Bourgeois ..................... 607/13 |
| 4,674,509 | A |   | 6/1987 | DeCote, Jr. ............ 128/419 PT |
| 4,727,877 | A | * | 3/1988 | Kallok ........................... 607/5 |
| 4,825,870 | A |   | 5/1989 | Mann et al. .......... 128/419 PG |
| 5,265,602 | A | * | 11/1993 | Anderson et al. ............... 607/9 |
| 5,391,188 | A | * | 2/1995 | Nelson et al. .................. 607/9 |
| 5,562,595 | A | * | 10/1996 | Neisz .......................... 600/16 |
| 5,662,689 | A | * | 9/1997 | Elsberry et al. ............... 607/5 |
| 6,337,996 | B1 |   | 1/2002 | Legay et al. .................... 607/9 |

FOREIGN PATENT DOCUMENTS

| EP | 0 962 235 A1 | 8/1999 |
| WO | WO 01/43819 A1 | 6/2001 |

\* cited by examiner

*Primary Examiner*—Scott M. Getzow
(74) *Attorney, Agent, or Firm*—Orrick Herrington & Sutcliffe LLP

(57) ABSTRACT

Detection of an evoked post-stimulation potential, in particular atrial potentials, in an active implantable medical device such as a cardiac pacemaker, a defibrillator, a cardioveter, or a multisite device. This device applies a stimulation pulse (40), then shorts-circuit for a discharge period (42, OCD) the output circuit, which includes discharging a connection capacitor, the self-impedance of the probe, and the impedance of the interface heart-electrode. A detection circuit includes an amplifier and a blanking circuit to temporarily uncouple the input terminal from the amplifier. A sequencer control circuit activates during a first time (micro blanking) the blanking circuit throughout the stimulation pulse (40), activates the discharging circuit with a delay after the application of the stimulation pulse, then inhibits the blanking circuit for a listening period (44), defining at least part of this delay, so as to authorize detection by the amplifier, during the listening period, of the evoked post-stimulation potentials, and then activates the blanking circuit a second time (BLANKING) after the listening period throughout the discharge period (42, OCD).

10 Claims, 4 Drawing Sheets

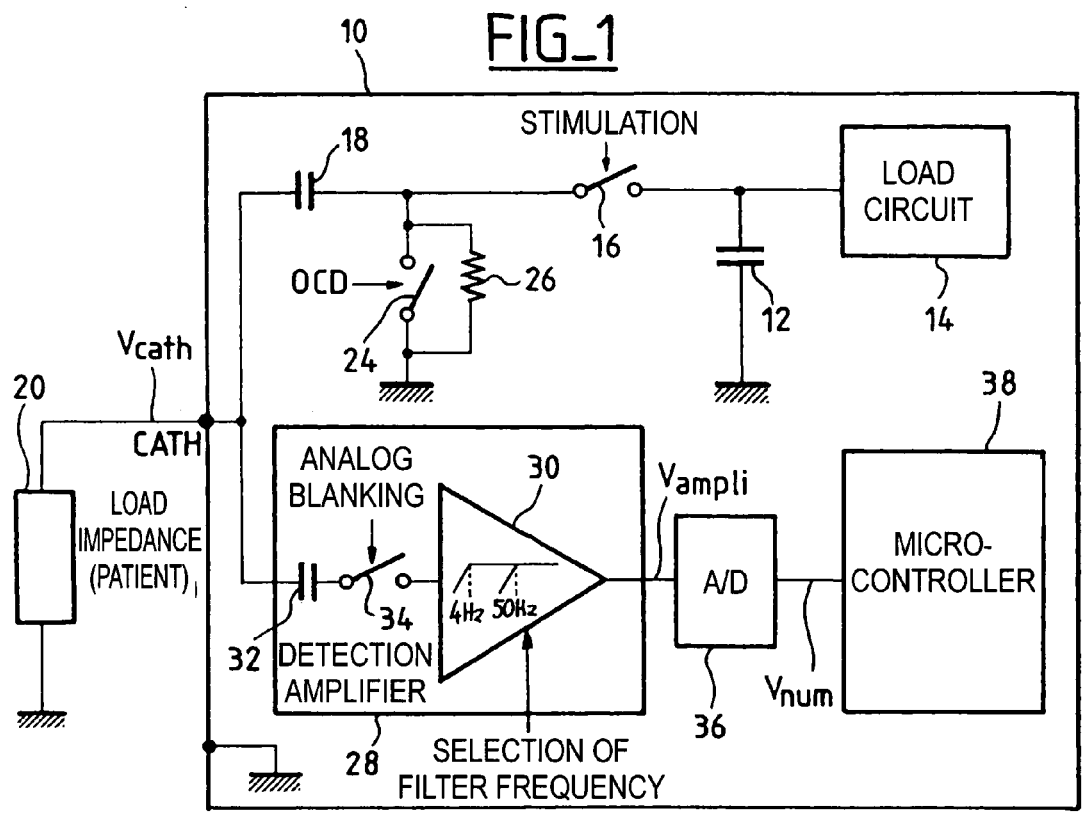
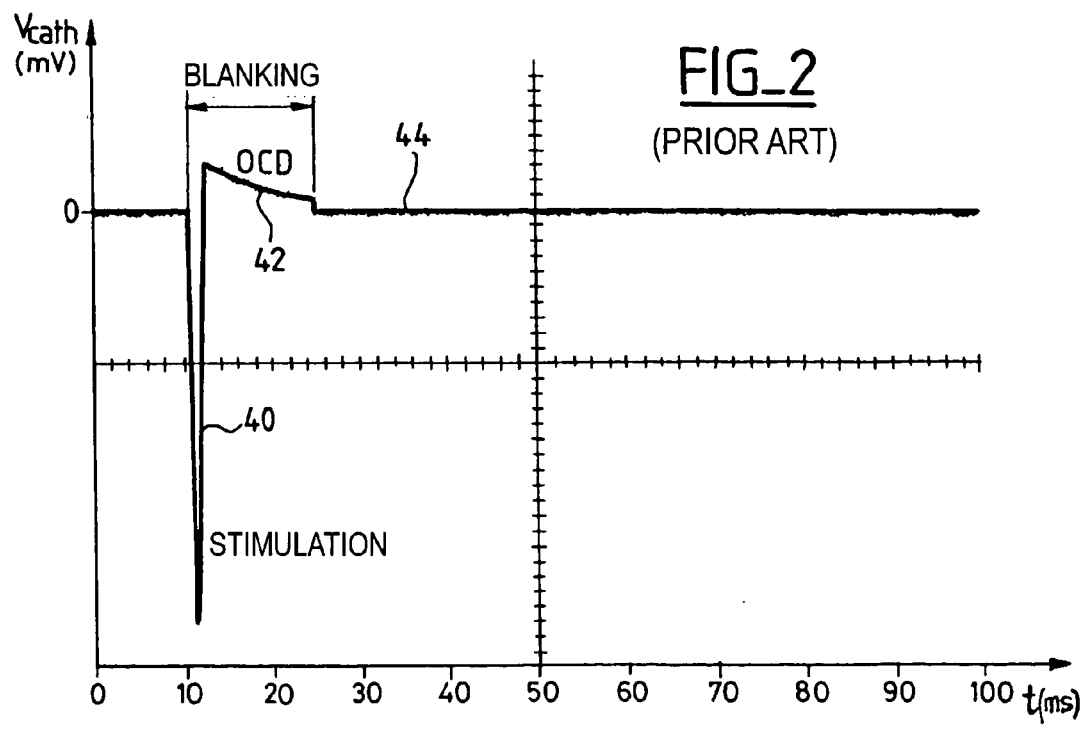

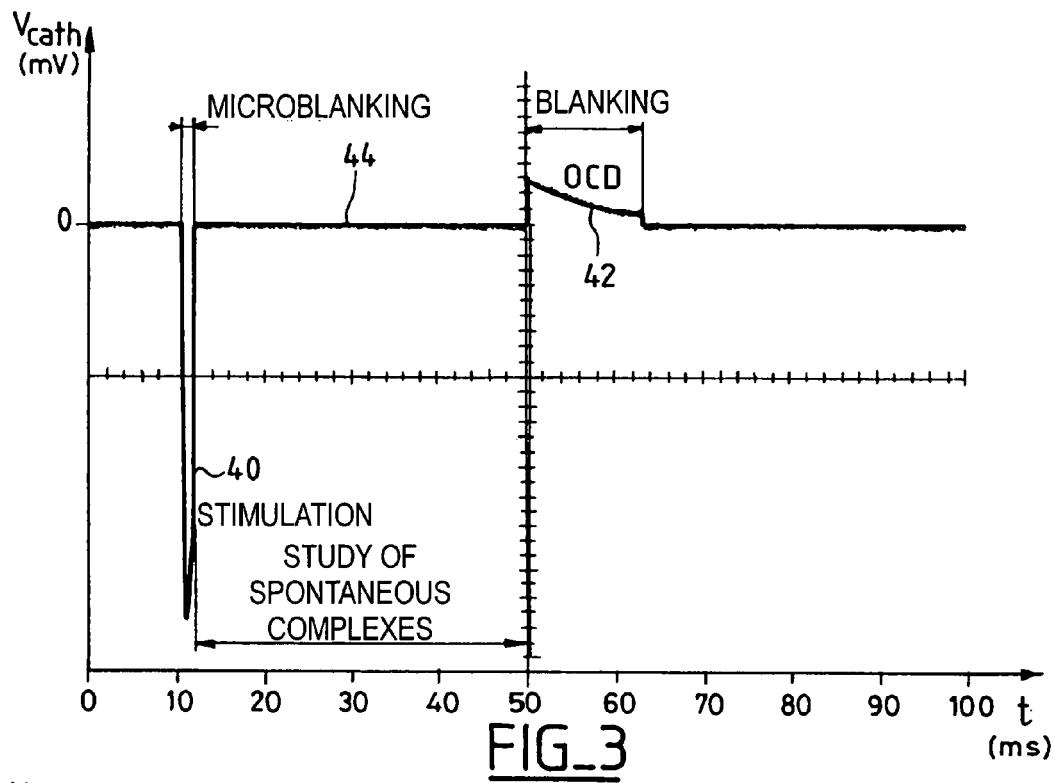
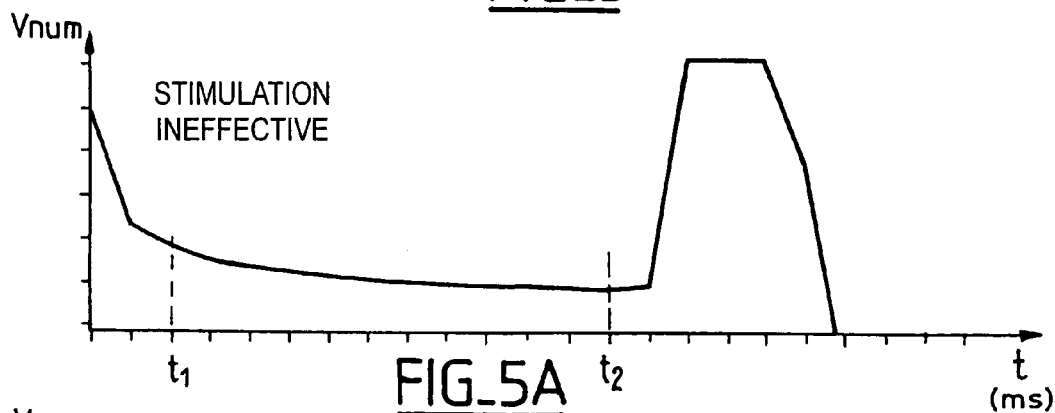
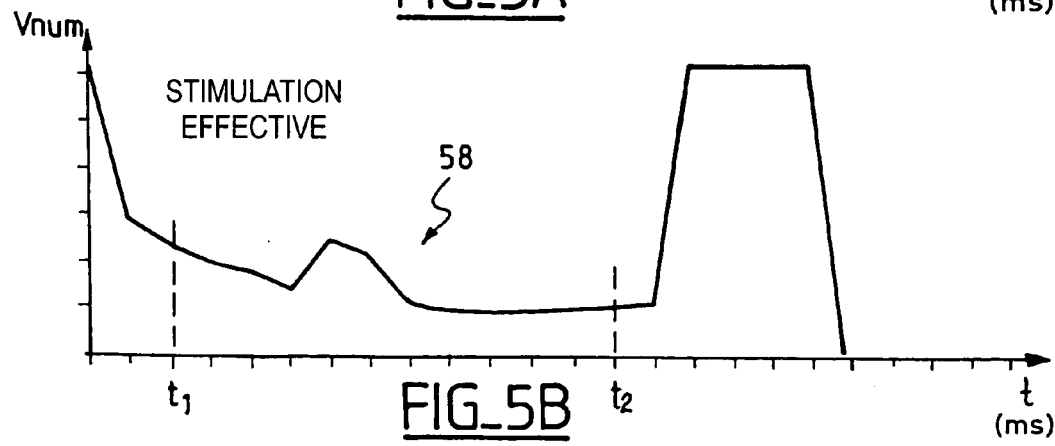

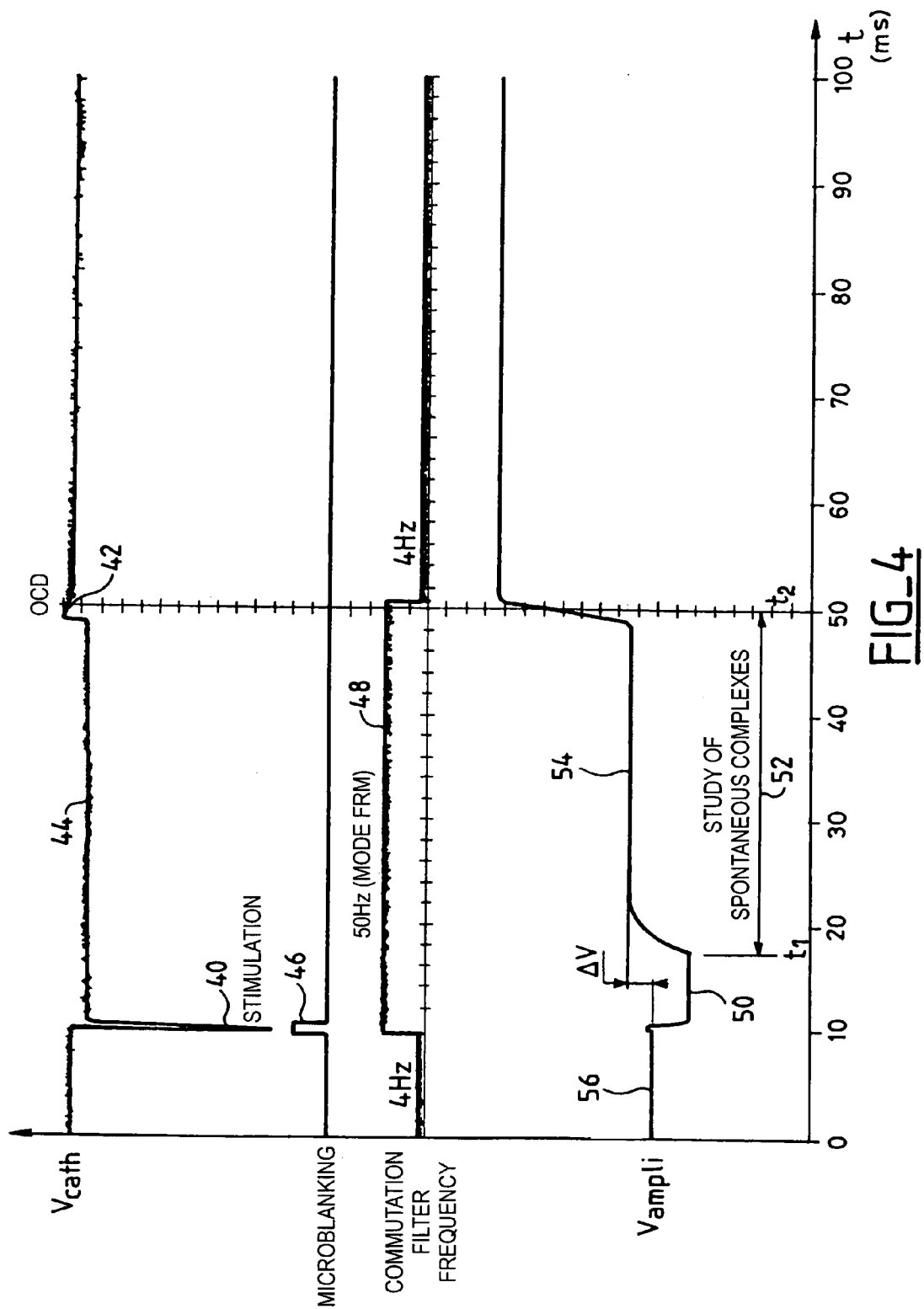
FIG_4

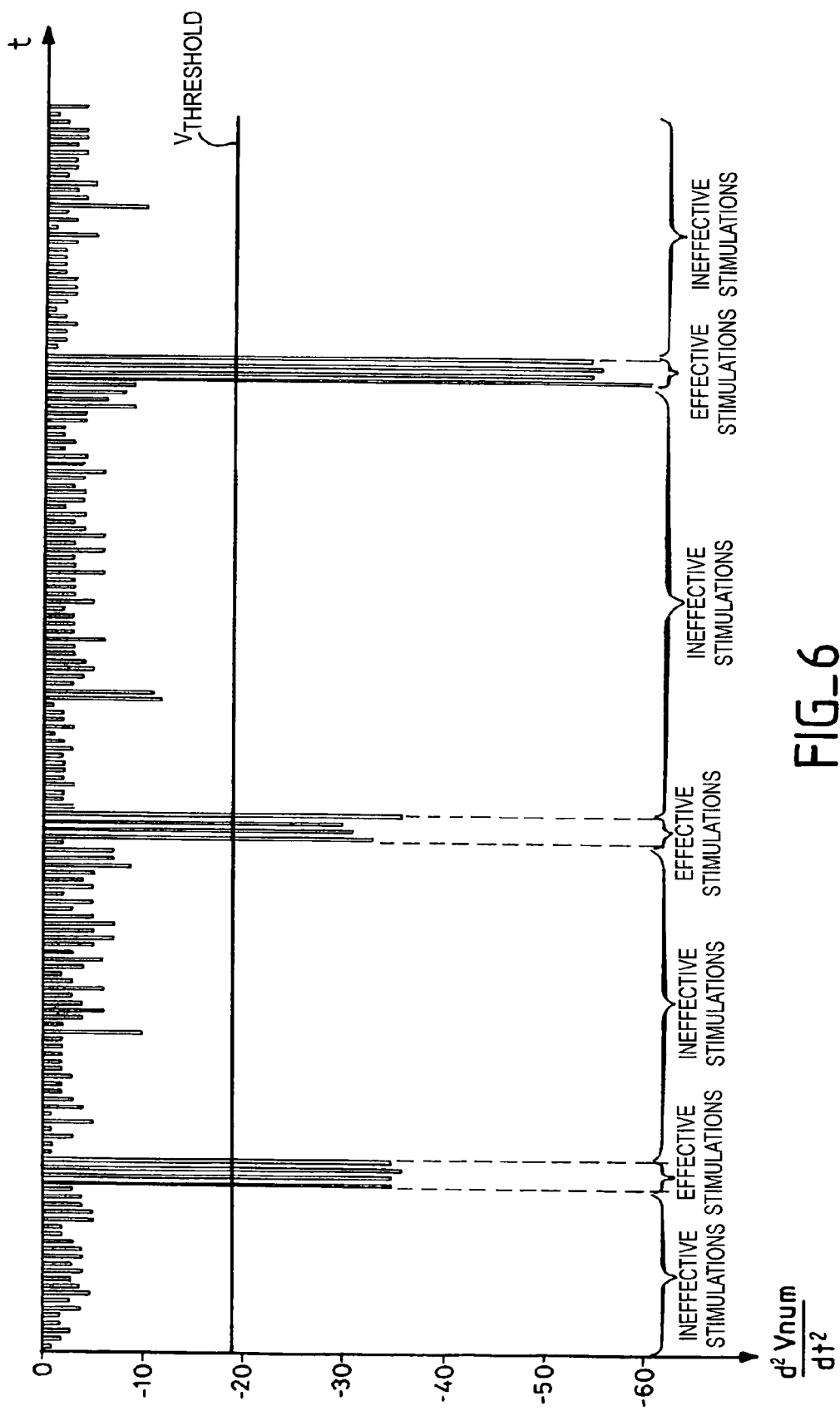
FIG_6

DETECTION OF EVOKED POST-STIMULATION POTENTIALS, IN PARTICULAR ATRIAL POTENTIALS IN AN ACTIVE IMPLANTABLE MEDICAL DEVICE SUCH AS CARDIAC PACEMAKER, DEFRIBILLATOR, CARDIOVERTOR OR MULTISITE DEVICE

FIELD OF THE INVENTION

The present invention relates to "active implantable medical devices" as such devices are defined by the Jun. 20, 1990 directive 90/385/CEE of the Council of European Communities, more precisely the devices known as cardiac pacemakers, defibrillators and/or cardiovertors that make it possible to deliver in the heart pulses of low energy for the treatment of the disorders of the cardiac rhythm.

BACKGROUND OF THE INVENTION

Active implantable medical devices include circuits for detecting cardiac activity, i.e., the detection of spontaneous depolarizations of the myocardium, as well as circuits for stimulating the myocardium, e.g., in the absence of a spontaneous depolarization. After a stimulation, it is important to be able to collect (sense) the "evoked wave", i.e., the depolarization wave that is induced by the stimulation of the considered cavity, in order to determine whether the stimulation was effective and, for example, to adjust the amplitude and/or the width of the stimulation pulse as appropriate to cause an effective depolarization.

One difficulty in this arises from the fact that the evoked wave is very early, i.e., it occurs very soon after the stimulation pulse is delivered and that at the detection amplifier output it is mixed in, and can be obscured with, an electric transient called the "amplifier response" consecutive to the electric stimulation. This amplifier response is always present independent of the presence or absence of an evoked wave, and depends only on the electric characteristics of the amplifier itself, of the energy contained in the stimulation pulse (amplitude and width), as well as of the impedance characteristics of the heart/electrode interface, called "load polarization".

In particular, to eliminate the electrical loads at the heart/electrode interface after a stimulation, one envisages to carry out a discharge of any accumulated energy. If this is not done, the following stimulations would end up not being effective. During the phase of discharge, it is envisaged to disconnect the amplifier inputs from the electrode terminal, which is known as a "blanking" of the detection circuits, typically for a length of time of about 14 ms, the stimulation pulse having a duration of about 1 ms. Moreover, at the time of the re-connection of the amplifier inputs to the terminals of the detection electrode at the end of the blanking period, a transitory rebound voltage appears at the amplifier output, which last a few milliseconds until the amplifier is completely de-saturated.

The study of the evoked wave is even more difficult in the case of an atrial stimulation. Indeed, an evoked atrial (P wave) wave has an amplitude that is much lower than in the case of the ventricle stimulation (R wave) and moreover occurs much sooner after stimulation: thus, the atrial evoked wave (P wave) appears approximately 10 ms after a stimulation to finish at approximately 30 ms, whereas the ventricular evoked wave (R wave) is observed approximately 60 ms after a ventricular stimulation.

One will understand that, under these conditions, it is very difficult to detect the presence of an evoked P wave, for example, in the case of an atrial capture test.

OBJECTS AND SUMMARY OF THE INVENTION

It is therefore, an object of the present invention to overcome this difficulty, by providing a new technique for the detection of the evoked P wave, taking into account its very early character and at the same time its low amplitude. A person of ordinary skill in the art will note, however, that the invention is not limited to the collection of the evoked P wave, but can be applied as well, taking into account the multiple advantages that it presents, to the collection of evoked R waves (ventricular waves), for example, in the case of a ventricular capture test.

As it will be described, the technique for the detection of the evoked wave according to the invention is independent of the load polarization of the probe, regardless of the energy level of the stimulation pulse, by allowing the detection of an eventual P wave during a first period, known as a "listening period", at the same time very early and prolonged, being able, for example, to extend typically from 6 ms to 40 ms after a stimulation if the stimulated cavity is the atrium.

One aspect of the present invention is directed to a device of type that includes, in a way in itself known, at least one circuit for delivering stimulation pulses to a cardiac cavity, at least one circuit for detecting the spontaneous potentials appearing in the aforementioned cavity, and a sequence control circuit as will be described. The circuit for delivering stimulation pulses applies a stimulation pulse to the cavity in a conventional manner via an intracardiac electrode of an implanted probe, connected at one end to a terminal of the device, and a discharging circuit that is able to short-circuit, for a discharge period, an output circuit that includes a capacitor coupled to the stimulation electrode, the self-impedance of the probe, and the impedance of the heart-electrode interface of the patient. The detection circuit comprises an amplifier, receiving at the input the signals at the device terminal as collected by the probe, and a blanking circuit able to temporarily uncouple the probe terminal from the amplifier input. The sequence control circuit is configured to, successively, activate the discharging circuit, after application of the stimulation pulse, throughout a discharge period, and activate the blanking circuit for at least the duration of the stimulation and the discharge period.

According to the invention, the sequencer control circuit is operated, moreover: to activate the blanking circuit a first time throughout the duration of the stimulation pulse; to activate the discharging circuit, with a delay after the application of the stimulation pulse; and then to inhibit the blanking circuit during a listening period defined by at least a part of the aforesaid delay, so as to authorize detection by the amplifier, during the listening period, of the spontaneous post-stimulation potentials in the considered cavity; then to activate the blanking circuit a second time, after the listening period, throughout the discharge period.

Advantageously, the amplifier is an amplifier commutable (switchable) between a mode of normal detection and a mode of fast desaturation, in particular having a filter operating with a low cut-off frequency mode and a high cut-off frequency mode respectively, and the sequencer control circuit is operated, moreover, to commutate (to switch) the amplifier to the fast desaturation mode throughout at least the listening period. Preferably, the sequencer control circuit re-commutates (switches back) the amplifier to the normal detection mode after the beginning of the discharge period, and in a manner nonconcomitant to the beginning.

Very advantageously, the sequencer control circuit operates to control the discharging circuit for a first length of time such that the discharge period finishes before the end of the post-stimulation refractory analysis period of the signal delivered by the amplifier, at the same time for the aforementioned cavity where the aforementioned post-stimulation spontaneous potentials are detected and for one or more cardiac cavities, so as to avoid false detection detections in this one or more cavities. This refractory period can in particular be a re-triggerable refractory period of a variable duration according to the level of disturbance present at amplifier output.

The device can comprise means for analyzing the signal delivered by the amplifier during the listening period, such that it is able to detect the presence of an evoked wave consecutive to the stimulation applied to the cavity, so as to discriminate between effective stimulations and non-effective stimulations. These means for analyzing can in particular comprise means for analyzing the variations of a derivative of order N, with N≦1, more preferably N=2, of the output signal delivered by the amplifier, in particular by detecting the crossing of a threshold by an extremum of this derivative.

BRIEF DESCRIPTION OF THE DRAWINGS

Further benefits, features and characteristics of the present invention will become apparent to a person of ordinary skill in the art in view of the following detailed description of a preferred embodiment of the invention, made with in reference to the annexed drawings, in which:

FIG. 1 is a schematic view of the stimulation and detection circuits implemented within the framework of a device in accordance with the present invention;

FIG. 2 illustrates a plot of the potential present on the stimulation electrode, within the framework of a prior art device;

FIG. 3 is homologous with FIG. 2, but for the device in accordance with the present invention;

FIG. 4 is a series of chronograms illustrating the sequence of the various operations of the device of FIG. 1 carried out in accordance with the teaching of the invention;

FIGS. 5A and 5B illustrate the potential variation at the detection amplifier output after digitalization of the signal, for an ineffective stimulation and an effective stimulation respectively; and FIG. 6 illustrates a clinical result illustrating the way in which it is possible to discriminate clearly between effective stimulations and ineffective stimulations by an analysis of the second derivative of the digitized signal in accordance with the present invention.

DETAILED DESCRIPTION OF THE INVENTION

With reference to FIG. 1, reference 10 indicates the device containing the various elements of the invention, with its circuit for delivering stimulation pulses, and its circuit for detection.

The circuit for delivering stimulation impulses comprises a tank capacitor 12 charged at a predetermined voltage by a load circuit 14. The energy accumulated in capacitor 12 is delivered for a predetermined time (duration of the stimulation pulse) by closing of a switch 16, ensuring the transfer of this energy via a connection capacitor 18, towards an output at terminal CATH of the pacemaker. This output terminal is connected, for example, to the distal probe electrode for an atrial or a ventricular stimulation. This probe and the electrode/myocardium interface has together an impedance schematized into load 20, constituting the load impedance of the device (including the series resistance of the probe and the cardiac tissue and the capacity of the interface, called "Helmholtz capacity").

Capacitor 18 has as its role to protect the patient against a possible D.C. current in the event of failure from the stimulation circuits, for example, of switch 16.

The stimulation pulse typically has an amplitude that is set at a value between 1.5 and 7.5 V, with a pulse width of between 0.12 ms and 0.98 ms (the stimulation energy is proportional to the width and the square of the amplitude of the pulse).

After application of a stimulation pulse, it is necessary to neutralize the loads accumulated in capacitor 18 and impedance load 20. This neutralization is operated by closing of a switch 24 electrically carrying out the serialization of the connection capacitor 18 of the device and impedance 20. This discharge operation, often indicated "OCD" (Output Capacitor Discharge), must be operated soon after a stimulation in order to cancel the average potential in the myocardium/electrode interface. If this is not the case, the stimulations following would quickly be made ineffective.

A resistance 26, typically of 200 kΩ, makes it possible to complete the discharge of capacitor 18 after reopening of switch 24. It also makes it possible to define the total input impedance of the apparatus for the detection of the cardiac signals. With regard to the detection circuit 28, it comprises an amplifier-filter 30 connected on terminal CATH via a connection capacitor 32 and a controlled switch 34. The $V_{ampli}$ signal at the output of amplifier 30 is sampled and digitized by an analog/digital converter (A/D) 36 delivering at its output a digitized signal $V_{num}$ able to be analyzed by the microcontroller 38 of the device.

The role of switch 34 is to ensure an analog "blanking", i.e., a disconnection of the input of amplifier 30 throughout the OCD and the stimulation durations, in order to avoid too significant a saturation. The voltages during stimulation can indeed reach several volts, with the voltage at the beginning of the OCD being on the order of a hundred millivolts.

The traditional manner to operate the blanking, as illustrated in FIG. 2, has the blanking period begin slightly before the pulse stimulation 40 and to finish slightly after the end of the OCD 42. For a typical OCD duration of 13 ms, the blanking duration is on the order of 14 ms so that the blanking period can completely enclose the stimulation duration and the OCD duration immediately following the stimulation.

After the OCD period 42, the potential at the input of amplifier is about stabilized, but at its output the amplifier still typically presents a transitory response to a post-blanking re-connection, thereby impairing any detection of an early evoked wave. In the case of an early evoked wave, particularly of a P wave (atrial) likely to arrive as early as 10 ms after stimulation, and in addition having a low amplitude and a short duration (typically from 10 to 15 ms), the evoked wave can be masked by the blanking operated for the period of blanking or during the post-blanking instability period described above, extending for about 15 to 20 milliseconds after the stimulation pulse. Indeed, a significant transient appears at the post-blanking re-connection at the amplifier output, which makes very difficult the detection of an atrial evoked wave of low amplitude, that is very early and very rapid.

Lastly, the OCD can be analyzed like a signal with a relatively low slope compared to the stimulation pulse, and with an amplitude very close to that of the endocardiac complexes: on this assumption, if the discharge of the interface is not completely finished at the end of the OCD—as is generally the case—the residual slow variation present on the catheter will be amplified in a significant way and will create a significant potential at the time of the post-blanking. This will prevent easily detecting the presence of a superimposed evoked cardiac potential.

The basic idea of the present invention, therefore, is directed to not immediately carrying out the OCD after stimulation, but instead shifting this phase of discharge to after the period of the evoked wave appearance.

This manner of proceeding is in particular illustrated in FIG. 3, where one can see that the listening period 44 is henceforth located before the period of OCD 42 instead of being after it. In the case of the search for a P wave, the shift of the OCD is typically approximately 40 ms after the stimulation of the atrium. In the case of the search for an R wave, the shift of the OCD after stimulation is larger (typically approximately 60 ms after the stimulation of the ventricle), because the R wave occurs less early than the P wave following the respective stimulations.

In all cases, the shift of the OCD must be such that the OCD takes place during the post-ventricular absolute refractory period or the post-atrial absolute refractory period (PVARP or PAARP), in order not to cause false detection of spontaneous complexes. This last constraint is, however, easy to respect, since the typical values of the absolute post-stimulation refractory periods are about 150 ms. Moreover, to avoid too large a saturation of the amplifier at the time of stimulation, a very short blanking or "micro-blanking" is carried out, beginning a few tens of microseconds before the beginning of the stimulation pulse, and finishing a few tens of microseconds after the end of this pulse. This micro-blanking also makes it possible to protect, if necessary, the analog input of the detection amplifier against any overload coming from the stimulation pulse.

In a preferential way, the micro-blanking protection is carried out by a component external to the integrated chip of the device, or by a distinct high voltage integrated circuit, whose intensity of integration (circuit density) can be less.

In addition, amplifier 30 used for detection is advantageously a commutable amplifier in a mode of fast desaturation, known as "FRM" (Fast Recovery Mode), before the stimulation pulse, this FRM mode being maintained during the study of the evoked wave. This commutation to a fast desaturation mode makes it possible for the amplifier to recover more quickly after the micro-blanking is carried out during stimulation, typically with a delay that is shorter than 8 ms.

Such a characteristic makes it possible to use a single detection amplifier for three different functionalities of the implantable cardiac prosthesis:

1. transmission of the endocardiac ECG, which must pass the low frequencies (from approximately 1 Hz);

2. the detection of the spontaneous cardiac signals inhibiting the pacemaker in a listening period (from approximately 25 Hz); and 3. the detection of the evoked waves very soon after the stimulation pulse (from approximately 50 Hz).

The FRM mode can be obtained in various ways, for example, by amplifying the polarization current of the amplifier, by re-setting certain internal networks to cancel the energy stored in the capacitive components, and/or, in a preferred embodiment as illustrated here, by increasing the cut-off frequency to a very high value, for example, 50 Hz.

The chronograms of FIG. 4 illustrate the sequencing of these various functions, while showing, from top to bottom:

1. the $V_{cath}$ voltages collected on terminal CATH of the device, successively showing the stimulation pulse 40, the listening period 44 of the evoked waves and the OCD (discharge) period 42;

2. the controlling of the micro-blanking by pulse 46 around the peak of stimulation 40; the commutation of the cut-off frequency of the amplifier (4 Hz in normal mode, 50 Hz in FRM mode), the step 48 corresponding to the duration during which the amplifier is commutated in FRM mode); and 3. the $V_{ampli}$ voltage collected at the detection amplifier output: after the inevitable transient response 50 during the first 8 milliseconds, the listening period 52 which is included between 8 and 40 ms is then free of any post-stimulation potential and makes it possible to detect without ambiguity the presence of an evoked complex.

The amplifier is left in mode FRM for all of listening period 44 of the evoked complex. The evoked signals are then transmitted at the detection amplifier output because they are very fast, and they will be treated within microcontroller 38 by a specific algorithm. In mode FRM, a sinusal ECG would be transmitted in a very deformed signal, and an atrial fibrillation would be very attenuated and thus difficult to detect.

For this reason, the detection amplifier is switched again to its normal listening mode for the detection of the spontaneous waves and the recording of the ECG, as soon as the period of study of the evoked complex is finished. It is at this time that the OCD can be triggered.

In a preferential way, the device leaves the mode FRM of the amplifier right after the beginning of the OCD (and not jointly at its beginning), in order not to link two types of disturbances. Indeed, the return from mode FRM to the normal mode will generate a significant disturbance at the amplifier output, and it is important to always return during a refractory time of the device. Preferably, one uses a re-triggerable refractory period system of which the duration is automatically adjusted according to the disturbance present at the detection amplifier output, such as that described, for example, in EP-A-0 962 235 and its corresponding U.S. Pat. No. 6,337,996 commonly assigned herewith to ELA Médical, which U.S. Patent is incorporated by reference herein in its entirety. In many cases, a duration of 150 ms for the refractory period remains sufficient for probes with average to low polarization.

In an advantageous way, a particular technique that can be used for the study of the evoked wave is as follows. As can be seen on the trace of the bottom of the chronogram of FIG. 4, the $V_{ampli}$ potential of the detection amplifier output during the period of study of spontaneous complexes 52 of the evoked wave includes a fast transient 50, recovered in approximately 10 ms, followed by an intermediate level of quasi-static potential 54. This intermediate potential level 54 is, however, different from the basic potential level 56 at rest. The absolute value of the intermediate potential 54 varies according to the nature of the probe and its polarization, so that the detection of the evoked wave cannot be done simply by detecting the crossing of a threshold by the $V_{ampli}$ signal at amplifier output. The system must thus be calibrated by evaluating regularly the level of the intermediate potential 54 during the life of the device.

An advantageous alternative to this calibration concerns analyzing samples of signal after digitalization to deduce therefrom a parameter. For example, and preferably as illustrated on the FIGS. 5A and 5B, a second derivative is evaluated between two programmable moments $t_1$ and $t_2$, during the study of spontaneous complexes period 52. A second derivative is easy to calculate when starting from digitized samples, so that this technique can be implemented in a simple way by a suitable known algorithm within microcontroller 38. As one can see it by comparing the FIGS. 5A and 5B, the evoked wave will appear very clearly with the examination of the digitized signal in the central zone. This wave 58, if it is present, appears in a very distinct manner.

FIG. 6 illustrates a clinical result with alternation of ineffective and effective stimulations. Effective stimulations (4 consecutive stimulations) give values of extrema (in fact minima) of the very large second derivative, whereas non-effective simulations give low values of these extrema. The criterion of detection of the evoked wave, i.e., the effectiveness of stimulation, results then simply from the crossing of a threshold value $V_{Threshold}$ of the second derivative. The cases where the second derivative crosses the threshold correspond undoubtedly to when the evoked P wave is present (FIG. 5B). On the other hand, when stimulation is ineffective (FIG. 5A) the second derivative remains well below the fixed threshold.

Suitable devices for which the present invention has application include, for example, the Talent™, Symphony™, and Rhapsody™, brand pacemakers and Alto™ brand of defibrillators, all available from Ela Médical, Montrouge France. These devices are microprocessor based systems with memory, data registers and the likes (microcontrollers) having circuits for receiving, conditioning and processing detected electrical signals, and are capable of receiving software instructions by telemetry, storing them in memory, and then executing those instructions to perform the functions described above in implementing the present invention. The creation of suitable software instructions for controlling an implant to perform the aforementioned functions of the present invention are believed to be within the abilities of a person of ordinary skill in the art. The detection circuits used to detect the cardiac signals in the atrium and the ventricular, in the left and/or right chambers, are well known and any suitable design may be used. Similarly, the switches used to open and close circuits for defined durations can be conventional transistor switches as are known to those skilled in the art, and may be integrated with the amplifier or included on associates structures, and controlled by bias voltages applied under microprocessor control.

One skilled in the art will appreciate that the present invention can be practiced by other than the described embodiments, which are presented for purposes of illustration and not of limitation.

We claim:

1. An active implantable medical device, in particular a cardiac pacemaker, defibrillator, cardiovertor or multisite device, comprising:
   a terminal having a receptacle for receiving an intracardiac electrode of an implanted probe, said probe having a distal end located in a first cardiac cavity;
   at least one circuit for delivering a stimulation pulse to said terminal;
   means for applying a stimulation pulse to said terminal for delivery to said first cardiac cavity;
   a discharging circuit coupled to said terminal having a switch operable to short-circuit for a discharge period said terminal;
   at least one circuit for detecting at said terminal electronic signals corresponding to spontaneous potential appearing in said first cardiac cavity, including
   an amplifier having an input coupled to said terminal and an output, and
   a blanking circuit having a switch able to temporarily uncouple the terminal from the amplifier input; and
   a sequencer control circuit to, successively within the same cardiac cycle:
      activate the discharging circuit in response to an application of the stimulation pulse, throughout the discharge period, and
      activate the blanking circuit for a first time throughout a detected stimulation pulse,
      activate the discharging circuit with a delay after the application of the stimulation pulse,
      inhibit the blanking circuit for a listening period, said listening period comprising at least a part of the said delay, wherein during this period of listening, the amplifier detects at said terminal, electric signals corresponding to spontaneous post-stimulation potentials in the first cavity; and
      activate the blanking circuit a second time after the listening period, throughout said discharge period.

2. The device of claim 1, wherein:
   said amplifier comprises a commutable amplifier having a normal detection mode and a fast desaturation detection mode, and
   the sequencer control circuit further comprises means for commutating the amplifier to operate in said fast desaturation mode throughout at least the listening period.

3. The device of claim 2, wherein the normal detection mode further comprises a low cut-off frequency and the fast desaturation mode further comprises a high cut-off frequency.

4. The device of claim 2, wherein the sequencer control circuit further comprises means for commutating the amplifier to operate in said normal detection mode after the beginning of the discharge period.

5. The device of claim 1, wherein the sequencer control circuit further comprises means for controlling the discharging circuit to terminate the discharge period before the end of a post-stimulation refractory period of analysis of the amplifier output signal.

6. The device of claim 5, wherein said sequencer control circuit terminates the discharge period before the end of the post-stimulation refractory period of analysis of the amplifier output signal, at the same time for the first cavity where said spontaneous post-stimulation potentials are detected and for at least a second cardiac cavity, so as to avoid false detections in said one or other cardiac cavities.

7. The device of claim 5, wherein said refractory period is a re-triggerable refractory period having a variable duration according to the level of disturbance present at amplifier output.

8. The device of claim 1, further comprising means for analyzing the amplifier output signal during the listening period, and detecting a presence of an evoked wave consecutive to an applied stimulation to said cavity, so as to discriminate between an effective stimulation and a non-effective stimulation.

9. The device of claim 8, wherein the means for analyzing further comprises means for analyzing a variation of a derivative of order N, with N being at least 1, of the amplifier output signal.

10. The device of claim 9, wherein the analyzing means further comprises means for detecting a crossing of a threshold by a extremum of the aforementioned N, order derivative of the amplifier output signal delivered by the amplifier.

* * * * *